United States Patent [19]

Shieh

[11] Patent Number: 5,784,434
[45] Date of Patent: Jul. 21, 1998

[54] DIGITAL INTRA-ORAL IMAGING SYSTEM FOR DENTAL RADIOGRAPHY

[75] Inventor: Yuh-Ren Shieh, Hsinchu, Taiwan

[73] Assignee: Industrial Technology Research Institute, Hsinchu, Taiwan

[21] Appl. No.: 784,425

[22] Filed: Jan. 16, 1997

[51] Int. Cl.$^6$ .................................................. A61B 6/14
[52] U.S. Cl. ........................................ 378/191; 378/98.8
[58] Field of Search ............................... 378/191, 168, 378/169, 170, 98.2, 98.3, 98.8

[56] References Cited

U.S. PATENT DOCUMENTS

| | | | |
|---|---|---|---|
| 1,555,430 | 9/1925 | Mortensen | 378/191 |
| 1,596,328 | 8/1926 | Wilt | 378/191 |
| 3,622,785 | 11/1971 | Irwin et al. | 378/191 X |
| 4,210,812 | 7/1980 | Ando et al. | 378/91 X |
| 4,987,307 | 1/1991 | Rizzo et al. | 378/191 X |

FOREIGN PATENT DOCUMENTS

| | | | |
|---|---|---|---|
| 0285214 | 10/1988 | European Pat. Off. | 378/191 |
| 681158 | 10/1950 | United Kingdom | 378/191 |

*Primary Examiner*—David P. Porta
*Attorney, Agent, or Firm*—Tung & Associates

[57] ABSTRACT

A low cost x-ray imaging system for dental radiography employs an intra-oral imaging device comprising a head portion insertable into a patient's mouth and a body portion forming a handle and containing a conventional solid state camera. The head portion employs low cost, commercially available components, including a flourescent film for converting x-ray images into visible light, and a prism or reflecting mirror for redirecting the visible image onto an image pickup such as a CCD array in the camera. The device outputs conventional RS-170 video signals which are processed by a conventional PC computer cooperating with a controller to control the timing and dosage of the x-rays received by the patient.

20 Claims, 1 Drawing Sheet

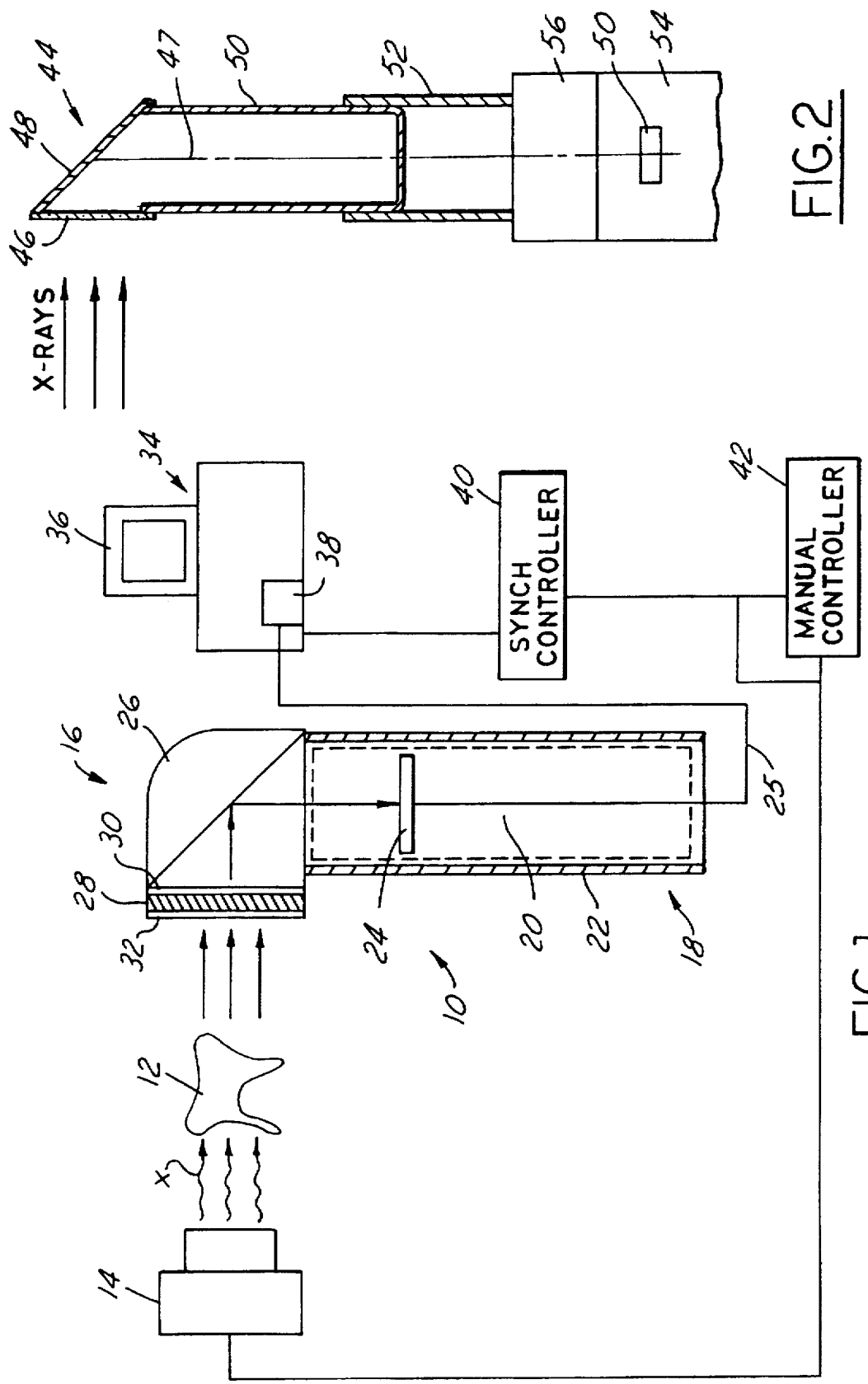

DIGITAL INTRA-ORAL IMAGING SYSTEM FOR DENTAL RADIOGRAPHY

FIELD OF THE INVENTION

The present invention generally relates to medical x-ray imaging systems, and deals more particularly with an x-ray imaging system for dental radiography useful in recording x-ray images of teeth without the use of film.

BACKGROUND OF THE INVENTION

X-ray apparatus has long been employed by dentists and oral surgeons for examining teeth prior to treatment. Film placed in a patient's mouth is posed to a source of x-rays which pass through the soft tissue of the skin and gums, and are absorbed or refracted by the harder tissue and teeth structures. The film is then chemically developed to produce an image from which the dentist makes appropriate decisions regarding treatment. Dental radiography employing film possesses numerous drawbacks, including the need for relatively high dosages of x-rays that are required in this process, the time, expense and uncertainty of processing x-ray films, and the problems associated with storing and disposing the developing chemicals.

In order to obviate the above mentioned problems associated with film type x-ray radiography, others have proposed systems for producing x-ray images without the need for film. These more recent, film-less x-ray imaging systems all employ means for converting the x-ray radiation into visible light through the use of scintillations, and conversion of the light into electronic video signals that are viewed on a display such as a CRT. The electronic video signals are typically derived from a solid state image pickup, such as a CCD (Charged Coupled Device) with a lens onto which visible light is focused which is then output by the scintillation. The image pickup devices employed by prior art, film-less dental radiography systems have been relatively complex and expensive, owing to the fact that the specially-designed pickup, along with the scintillation (typically a flourescent material and optical fiber) are packaged into a compact device which is inserted into an intra-oral region of the patient's mouth, behind a tooth to be x-rayed. This arrangement has created the need for specialized, miniaturized devices which place the image pickup in close proximity to the layer of flourescent material.

While certain of the above described miniaturized video x-ray systems have been effective, they have not gained wide-spread use because of their complexity and cost. Accordingly, there is a clear need in the art for a simple, low cost video signal type imaging system for dental radiography which can be manufactured using readily available, low cost components. The present invention is directed towards satisfying this need.

SUMMARY OF THE INVENTION

According to the present invention a film-less, x-ray system for dental radiography includes an intra-oral imaging device coupled with a video signal display, a source of x-ray and a controller which controls the x-ray source (and thus the timing and dosage of the x-rays applied to the tooth), and a computer for processing the video signals and displaying the recorded image on a CRT or the like.

In one embodiment, the intra-oral imaging device includes a head portion containing certain optical elements, and a body portion which both houses a solid state camera and functions as a handle to allow manipulation of the head within the intra-oral region of a patient's mouth. The head portion includes a layer of flourescent material, in the form of a film sandwiched between two x-ray transparent sheets of material, such as glass. X-ray images passing through the tooth impinge upon the flourescent film which converts these x-rays into visible light energy corresponding to an image of the tooth. A prism element mounted within the head redirects the light energy 90 degrees into the body portion of the device. The redirected light energy is focused onto a solid state image pickup, such as a CCD, forming part of a commercially available, low cost pen type camera contained entirely within the body. The video signals output by this video camera are in a conventional RS-170 format, and are delivered to a PC type computer which processes the signals and displays the tooth image on a suitable display, such as a CRT.

In an alternate form of the invention, the head portion employs a simple mirror to redirect the image from the flourescent film to a solid state camera where the image is converted to video signals. In this embodiment, the head portion may be arranged in a smaller package which is fitted to the end of a video camera.

Accordingly, it is a primary object of the present invention to provide an x-ray image system for dental radiography which avoids the use of film and employs low-dose x-rays and low-cost, commonly available components.

A further object of the invention is to provide a system as described above which employs an intra-oral imaging device having a head which may be inserted into an intra-oral region behind a tooth, which employs a conventional optical element for redirecting light energy into a conventional camera.

A further object of the invention is to provide an imaging system as described above wherein the intra-oral device integrates the miniature camera into the handle of the device.

These, and further objects and advantages of the present invention will be made clear or will become apparent during the course of the following description of a preferred embodiment of the present invention.

BRIEF DESCRIPTION OF THE DRAWINGS

In the drawings, which form an integral pan of the specification, and are to be read in conjunction therewith, and in which like reference numerals designate like components in the various views:

FIG. 1 is combined schematic and diagrammatic view of an x-ray imaging system for dental radiography in accordance with one embodiment of the invention; and, FIG. 2 is a cross sectional, diagrammatic view of a portion of an alternate embodiment of the intra-oral imaging device.

DESCRIPTION OF THE PREFERRED EMBODIMENT

Referring first to FIG. 1, the present invention involves a hand held intra-oral imaging device, generally indicated by the numeral 10, for performing dental radiography without the use of film. A head portion 16 of the device 10 is inserted into an intra-oral region of a patient's mouth, behind a tooth 12 for example, which is irradiated with a conventional source of x-rays 14. X-rays emanating from the source 14 pass through the soft bone and tissue area of the patient's mouth, thence through the tooth 12, onto an imaging area of the head portion 16. In the case of the embodiment illustrated in FIG. 1, this imaging area is relatively small, for example 2×3 centimeters.

The x-ray image of the tooth 12 is received on the face of a layer of flourescent material which, in the illustrated embodiment, comprises a film 28 of flourescent material sandwiched between a pair of protective transparent sheets 30, 32 which may be glass plates, for example. The flourescent film converts the x-ray image into protons or light energy in the visible range thereby forming a visible image of the tooth 12. This visible image is directed into a conventional, 45 degree prism 26 which redirects the image 90 degrees into an elongated body portion 18 which forms a handle for manipulating the head portion 16 within the patient's mouth. The body portion 18 includes an outer, cylindrical housing 22 formed of a material which is impervious to the x-rays. Within the housing 22, there is mounted a miniaturized, conventional solid state pen camera 20 which includes an image pickup device in the form of a CCD (Charged Coupled Device) two dimensional array 24. Inasmuch as the pen camera 20 is a well known commercial device, the various details thereof, including lenses and electronics are not shown in the drawing.

The image pickup 24 is positioned much that the visible image redirected by the prism 26 impinges upon the photosensitive surface of the pickup 24 thereby forming an image thereon. Typically, the pickup 24 will have a resolution of 512 horizontal scan lines, add 600 vertical lines, and is capable of recording an image less than 1/10 of a second. Video signals corresponding to the image recorded on the pickup 24 are output in the form of conventional RS-170 signals on line 25 which connects the device and to a conventional computer 34. The computer 34 may be of a conventional desk-top, PC type which includes a CRT display 36, and an image grabber card 38 that stores data corresponding to the recorded image of the tooth 12. The computer 34 is connected with a synchronous controller 40 which is responsive to the computer 34 for controlling the x-ray source 14. Specifically, the synchronous controller 40 controls the exposure time (and thus the dosages) of the x-rays x delivered from the source 14 to the tooth 12. A manual controller 42, such as a button or switch connected between the synchronous controller 40 and the x-ray source 14 may be employed to further control the timing and operation of the x-ray source 14. As mentioned previously, the controllers 40 and 42, operating in concert with the computer 34 control the x-ray source 14 such that the exposure time of the tooth 12 to the x-rays is as little as 1/30 of a second. This compares to an exposure time of approximately 1.2 seconds for systems employing conventional film. Thus, by employing the system of the present invention, the patient is exposed to approximately 1/10 of the dosage of x-rays that would normally be used in a film type dental radiography system.

All of the components described above are readily available, low-cost items commercially available on the market, and are thus easily maintained and have high reliability. Specialized computers and controllers are not required due to the fact that a conventional pen camera 20 is used which outputs standard RS-170 signals which are easily processed using conventional PC computers.

The head portion 16 may be easily removed from the body portion 18 in order to perform maintenance, repairs, replacements or cleaning. The head portion 16 is detachably secured to the body portion 18 by means of a threaded interconnection, bayonet mount or the like (not shown). Since the head portion 16 is readily detachable, a number of differently configured or sized head portions 16 may be interchangeably mounted on the same body portion 18, in order to tailor the device 10 for specific kinds of examinations within the mouth.

Attention is now directed to FIG. 2 wherein an intra-oral image device is 10a is depicted which forms an alternate embodiment of the present invention. The device 10a includes a head portion 44 comprising a plate 46 of flourescent material and a reflecting mirror 48, (which may be either circular or rectangular in shape) positioned at approximately a 45 degree angle to the optical axis of the flourescent plate 46. X-rays impinging on the flourescent plate 46 are converted into visible energy that is focused on to the reflecting surface of the reflected mirror 44 which reflects and therefore redirects the light 45 degrees along a central optical axis 47 through an extension tube 50 which allows the head portion 44 to be inserted into the appropriate intra-oral region of the patient's mouth. The extension tube 50 is attached to a conventional solid state camera 54 by means of an adapter 52, such that the image reflected by mirror 48 passes through the camera lens 56 and is focused onto a CCD image pickup 58 of the camera 54. The embodiment shown in FIG. 2 is particularly simple and economical to construct inasmuch as the head portion 44 is of extremely simple construction and can be easily mounted onto the end of a conventional solid state camera 54.

From the foregoing, it can be appreciated that the present invention reliably provides for the accomplishment of the objects of the invention and does so in a particularly simple and economical manner. It is recognized, or course, that those skilled in the art may make various modifications or additions to the preferred embodiment chosen to illustrate the invention without departing from the spirit and scope of the present contribution to the art. Accordingly, it is to be understood that the protection sought to be afforded hereby should be deemed to extend to the subject matter claimed and all equivalents thereof fairly within the scope of the invention.

I claim:

1. An x-ray imaging system for dental radiography, comprising:

an intra-oral imaging device including a body and a head connected to said body, said head being adapted to be disposed in an intra-oral region behind a tooth, said head including a layer of material for converting x-rays passing through said tooth along a first axis into a visible image, and an optical element for redirecting said visible image along a second axis, said device further including a camera having a solid state image pickup for recording said visible image redirected by said optical element without an optical system placed thereinbetween, means for displaying the visible image recorded by said pickup;

a source of x-rays, and, a controller operably connected with said display means, said imaging device and said x-ray source for controlling the operation of said x-ray source.

2. The imaging system of claim 1, wherein said layer of material includes a flourescent film.

3. The imaging system of claim 2, wherein said device includes a pair of transparent sheets and said layer of material is sandwiched between said sheets.

4. The imaging system of claim 1, wherein said device includes a pair of glass sheets and said layer of material is sandwiched between said glass sheets.

5. The imaging system of claim 4, wherein said layer of material includes a flourescent material.

6. The imaging system of claim 1, wherein said optical element is a prism.

7. The imaging system of claim 1, wherein said optical element is a mirror.

8. The imaging system of claim 1, wherein said camera is contained in said body portion and said body portion forms a handle for manipulating said head portion within said intra-oral region.

9. The imaging system of claim 1, wherein said controller includes manually operable control means for controlling the timing and amount of x-rays delivered by said x-ray source to said tooth.

10. The imaging system of claim 1, wherein said body includes an outer housing formed of a material impervious to x-rays, and said camera is contained within said housing.

11. An x-ray imaging device for dental radiography, comprising:

a main body portion defining a handle, a head portion on one end of said body, portion, said head portion being adapted to be disposed in an intra-oral region behind a tooth, said head portion including
  (1) a medium for converting x-rays passing through said tooth into light energy, corresponding to a visible image,
  (2) an optical element for redirecting said light energy from said head into said body portion, and, a solid state image pickup in said body portion for receiving said light energy directly from said head and converting said light energy into electronic data representing said image.

12. The imaging system of claim 11, wherein said medium includes a layer of flourescent material.

13. The imaging device of claim 12, wherein said head portion includes a pair of transparent plates and said flourescent material is a film sandwiched between said plates.

14. The imaging device of claim 11, wherein said optical element is a prism.

15. The imaging device of claim 11, wherein said optical element is a mirror.

16. The imaging device of claim 11, wherein said body portion includes a camera and said pickup forms a part of said camera.

17. The imaging device of claim 16, wherein said body portion includes an outer housing formed of a material substantially impervious to x-rays.

18. The imaging device of claim 11, wherein said medium and said image pickup respectively have orthogonal, optical axis.

19. The imaging device of claim 11, wherein said pickup forms a portion of a pen camera fully contained within said body portion.

20. The imaging device of claim 11 including a barrel connecting said head portion and said body portion, and a lens for focusing said light energy onto said pickup.

* * * * *